(12) United States Patent
Sakon et al.

(10) Patent No.: US 6,676,968 B1
(45) Date of Patent: Jan. 13, 2004

(54) RELEASE-REGULATING PREPARATIONS COMPRISING BIPHENYLDIAMINE DERIVATIVES

(75) Inventors: Kiyoyuki Sakon, Tokyo (JP); Masahiko Narasaki, Tokyo (JP); Kentaro Fujinaga, Tokyo (JP); Yoji Yamamoto, Tokyo (JP); Hiroaki Mitsuhashi, Tokyo (JP); Kazuoki Tsuruta, Tokyo (JP); Hirofumi Tanabe, Tokyo (JP); Yoshiaki Igarashi, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/889,487

(22) PCT Filed: Jan. 25, 2000

(86) PCT No.: PCT/JP00/00353
§ 371 (c)(1),
(2), (4) Date: Jul. 18, 2001

(87) PCT Pub. No.: WO00/44380
PCT Pub. Date: Aug. 3, 2000

(30) Foreign Application Priority Data

Jan. 28, 1999 (JP) .............................. 11-19815

(51) Int. Cl.[7] .................. A61K 9/22; A01N 43/40
(52) U.S. Cl. ................. 424/468; 424/480; 424/482; 514/331; 514/317; 546/192; 546/229
(58) Field of Search ................. 514/331, 317; 546/192, 229; 424/468, 474, 480, 482

(56) References Cited

U.S. PATENT DOCUMENTS

| | | | | |
|---|---|---|---|---|
| 5,597,825 A | * | 1/1997 | Himmelsbach et al. | ..... 514/255 |
| 5,736,559 A | * | 4/1998 | Himmelsbach et al. | ..... 514/330 |

FOREIGN PATENT DOCUMENTS

| JP | 4-334351 | 11/1992 |
|---|---|---|
| JP | 6-50977 | 2/1994 |
| JP | 9-2977 | 1/1997 |
| JP | A 9-2977 | 7/1997 |
| JP | 10-1467 | 1/1998 |
| JP | WO 98/03202 | 1/1998 |
| JP | A 10-231254 | 2/1998 |
| JP | 10-231254 | 9/1998 |
| WO | 98/03202 | 1/1998 |
| WO | 99/26918 | 6/1999 |
| WO | 99/26919 | 6/1999 |

OTHER PUBLICATIONS

Chemical Abstracts: 131:5191. Hara et al. Jun. 1999.*

Yoshihisa Matsuda, ed. "Iyakuhin Tenkazai Yoran", Nov. 25, 1992. Yakuji Jihosha, pp 24–45.

* cited by examiner

*Primary Examiner*—Thurman K. Page
*Assistant Examiner*—Lakshmi Channavajjala
(74) *Attorney, Agent, or Firm*—Sughrue Mion, PLLC

(57) ABSTRACT

A medicinal composition containing one or more compounds selected from the compounds represented by the following formula (I), salts of these compounds, solvates of these compounds and solvates of these salts and being capable of reducing the contact of the compounds with the components in the bile or pancreatic juice.

Formula (I)

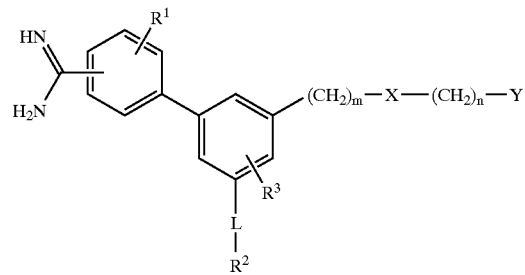

6 Claims, No Drawings

RELEASE-REGULATING PREPARATIONS COMPRISING BIPHENYLDIAMINE DERIVATIVES

TECHNICAL FIELD

The present invention relates to medicinal compositions containing a new compound.

More particularly, the invention relates to medicinal compositions effective for improving the absorption of said new compound through digestive tracts by reducing the contact of the compound with components of bile or pancreatic juice secreted in the duodenum.

BACKGROUND ARTS

Medicinal compositions added with cyclodextrins and lipophilic substances such as medium-chain fatty acid triglycerides were disclosed in the specifications of the JP-A 9-2977 (hereinafter, JP-A means "Japanese Unexamined Patent Application".) and JP-A 10-231254 as the compositions to improve the absorption of aromatic amidine derivatives through the digestive tracts. However, the long-term safety of cyclodextrins administered by peroral administration is not sufficiently confirmed and the lipophilic substance such as medium-chain triglyceride is possible to cause the adverse effects on the digestive tracts such as diarrhea and the risk of the failure in the barrierness of the digestive tract membrane. Further, the absorption-improving effect shown in these inventions is not expectable to be selective to the compound and have high safety. Specification of WO 98/3202 disclosed a medicinal composition containing an anion exchange resin with respect to aromatic amidine derivatives. However, cholestyramine shown as a preferable example of anion exchange resin in the specification is the active component itself used as a medicine for hyperlipemia and the substance is not expectable as a preferable material from the safety point of view owing to its new physiological action.

No proposal has been made on medicinal compositions containing the compound of the present invention to improve the absorption through the digestive tracts by reducing the contact with the components in the bile or pancreatic juice.

The object of the present invention is to provide medicinal compositions containing the compound of the present invention.

Another object of the present invention is to provide medicinal compositions containing the compound of the present invention and effective for improving the absorption through the digestive tracts by reducing the contact of the compound with the components in the bile or pancreatic juice in the case of peroral administration.

DISCLOSURE OF THE INVENTION

The present invention provides medicinal compositions containing one or more compounds selected from the compounds represented by the following formula (I), salts of these compounds, solvates of these compounds and solvates of these salts (hereinafter collectively called as "the compounds of the present invention" in some cases) and being capable of reducing the contact of the compounds with the components in the bile or pancreatic juice.

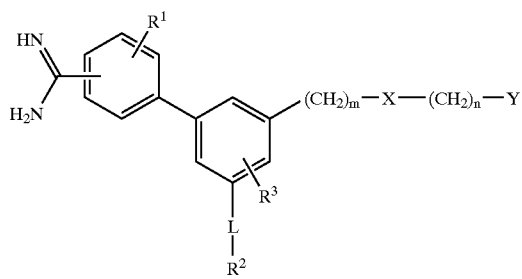

Formula (I)

[in the Formula (I), $R^1$ is hydrogen atom, fluorine atom, chlorine atom, bromine atom, hydroxyl group, amino group, nitro group, a $C_1$–$C_8$ alkyl group or a $C_1$–$C_8$ alkoxy group, L is direct bond or a $C_1$–$C_4$ alkylene group, $R^2$ is fluorine atom, chlorine atom, bromine atom, hydroxyl group, amino group, a $C_1$–$C_8$ alkoxy group, carboxyl group, a $C_1$–$C_8$ alkoxycarbonyl group, an aryloxycarbonyl group, an aralkoxycarbonyl group, carbamoyl group (the nitrogen atom constituting the carbamoyl group may be substituted with mono- or di-$C_1$–$C_8$ alkyl group or may be the nitrogen atom of an amino acid), a $C_1$–$C_8$ alkylcarbonyl group, a $C_1$–$C_8$ alkylsulfenyl group, a $C_1$–$C_8$ alkylsulfinyl group, a $C_1$–$C_8$ alkylsulfonyl group, a mono- or di-$C_1$–$C_8$ alkylamino group, a mono- or di-$C_1$–$C_8$ alkylaminosulfonyl group, sulfo group, phosphono group, bis(hydroxycarbonyl)methyl group, a bis(alkoxycarbonyl)methyl group or 5-tetrazolyl group, $R^3$ is hydrogen atom, fluorine atom, chlorine atom, bromine atom, hydroxyl group, amino group, nitro group, a $C_1$–$C_8$ alkyl group, a $C_1$–$C_8$ alkoxy group, carboxyl group or a $C_1$–$C_8$ alkoxycarbonyl group, X is a group of the formulas —O—, —S—, —SO—, —SO$_2$—, —NH—CO—NH—, —N($R^4$)—, —CO—N($R^5$)—, —N($R^5$)—CO—, —N($R^5$)—SO$_2$— or —SO$_2$—N($R^5$)— (in the formulas, $R^4$ is hydrogen atom, a $C_1$–$C_{10}$ alkyl group, a $C_1$–$C_{10}$ alkylcarbonyl group, a $C_1$–$C_{10}$ alkylsulfonyl group, a $C_3$–$C_8$ cycloalkyl group or an aryl group, $R^5$ is hydrogen atom, a $C_1$–$C_{10}$ alkyl group, a $C_3$–$C_8$ cycloalkyl group or an aryl group (the alkyl groups of $R^4$ and $R^5$ may be substituted with an aryl group, hydroxyl group, amino group, a halogen atom, a $C_1$–$C_8$ alkoxy group, carboxyl group, a $C_1$–$C_8$ alkoxycarbonyl group, an aryloxycarbonyl group, an aralkoxycarbonyl group, carbamoyl group or 5-tetrazolyl group), Y is a $C_4$–$C_8$ cycloalkyl group (in the above ring system, the methylene group may be replaced with carbonyl group and the ring system may be substituted with fluorine atom, chlorine atom, bromine atom, hydroxyl group, amino group, a $C_1$–$C_8$ alkyl group, a $C_1$–$C_8$ alkoxy group, carbamoyl group, a $C_1$–$C_8$ alkoxycarbonyl group, carboxyl group, an aminoalkyl group, a mono- or di-alkylamino group or a mono- or di-alkylaminoalkyl group), or a 5- to 8-membered ring group of the following formulas I-1 or I-2

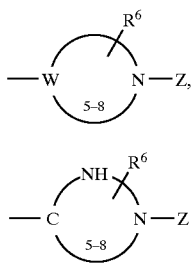

Formula (I-1)

Formula (I-2)

(in the formulas I-1 and I-2, the methylene group of each ring system may be replaced with carbonyl group and unsaturated bond may be present in the ring, $R^6$ is hydrogen atom, fluorine atom, chlorine atom, bromine atom, hydroxyl group, amino group, nitro group, a $C_1$–$C_8$ alkyl group or a $C_1$–$C_8$ alkoxy group, W is C—H or nitrogen atom (W is not nitrogen atom when the ring is a 5-membered ring), Z is hydrogen atom, a $C_1$–$C_{10}$ alkyl group (the alkyl group may be substituted with hydroxyl group (excluding the case of $C_1$ alkyl group), amino group, a $C_1$–$C_8$ alkoxy group (excluding the case of $C_1$ alkyl group), carboxyl group, a $C_1$–$C_8$ alkoxycarbonyl group, an aryloxycarbonyl group or an aralkoxycarbonyl group), a $C_1$–$C_8$ alkylcarbonyl group, an arylcarbonyl group, an aralkylcarbonyl group, amidino group or a group of the following formula I-3

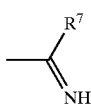

Formula (I-3)

(in the Formula I-3, $R^7$ is a $C_1$–$C_8$ alkyl group (the alkyl group may be substituted with hydroxyl group or a $C_1$–$C_8$ alkoxy group), an aralkyl group or an aryl group), m is an integer of from 1 to 3, and n is an integer of from 0 to 3 (when n is 0 or 1, W is not nitrogen atom)].

BEST MODE FOR CARRYING OUT THE INVENTION

The present invention is explained in more detail by the following description.

In the above definition of the substituent of the compound of the general formula (I) of the present invention, the "$C_1$–$C_8$ alkyl group" means a straight or branched carbon chain having 1 to 8 carbon atoms, for example, methyl group, ethyl group, propyl group, isopropyl group, butyl group, isobutyl group, tert-butyl group, pentyl group, neopentyl group, isopentyl group, 1,2-dimethylpropyl group, hexyl group, isohexyl group, 1,1-dimethylbutyl group, 2,2-dimethylbutyl group, 1-ethylbutyl group, 2-ethylbutyl group, isoheptyl group, octyl group or isooctyl group, preferably a group having a carbon number of from 1 to 4, especially preferably methyl group or ethyl group.

The "$C_1$–$C_8$ alkoxy group" means an alkoxy group having a carbon number of from 1 to 8, concretely methoxy group, ethoxy group, propoxy group, isopropoxy group, butoxy group, isobutoxy group, sec-butoxy group, tert-butoxy group, pentyloxy group, neopentyloxy group, tert-pentyloxy group, 2-methylbutoxy group, hexyloxy group, isohexyloxy group, heptyloxy group, isoheptyloxy group, octyloxy group, isooctyloxy group, etc., preferably a group having a carbon number of from 1 to 4, especially preferably methoxy group or ethoxy group.

The "$C_1$–$C_4$ alkylene" means a straight-chain alkylene having a carbon number of from 1 to 4 and is methylene, ethylene, propylene or butylene.

The "$C_1$–$C_8$ alkoxycarbonyl group" means methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, hexyloxycarbonyl group, heptyloxycarbonyl group, octyloxycarbonyl group, etc., preferably methoxycarbonyl group, ethoxycarbonyl group or tert-butoxycarbonyl group, more preferably methoxycarbonyl group.

The "aryloxycarbonyl group" means phenoxycarbonyl group, naphthyloxycarbonyl group, 4-methylphenoxycarbonyl group, 3-chlorophenoxycarbonyl group, 4-methoxyphenoxycarbonyl group, etc., preferably phenoxycarbonyl group.

The "aralkoxycarbonyl group" means benzyloxycarbonyl group, 4-methoxybenzyloxycarbonyl group, 3-trifluoromethylbenzyloxycarbonyl group, etc., preferably benzyloxycarbonyl group.

The "amino acid" means natural or non-natural commercially available amino acids, preferably glycine, alanine or β-alanine, more preferably glycine.

The "$C_1$–$C_8$ alkylcarbonyl group" means a carbonyl group having straight or branched carbon chain having a carbon number of from 1 to 8, e.g. formyl group, acetyl group, propionyl group, butyryl group, isobutyryl group, valeryl group, isovaleryl group, pivaloyl group, hexanoyl group, heptanoyl group and octanoyl group, preferably a carbonyl group having a carbon number of from 1 to 4, more preferably acetyl group or propionyl group.

The "$C_1$–$C_8$ alkylsulfenyl group" means an alkylsulfenyl group having a carbon number of from 1 to 8, concretely methylthio group, ethylthio group, butylthio group, isobutylthio group, pentylthio group, hexylthio group, heptylthio group, octylthio group, etc., preferably methylthio group.

The "$C_1$–$C_8$ alkylsulfinyl group" means an alkylsulfinyl group having a carbon number of from 1 to 8, concretely methylsulfinyl group, ethylsulfinyl group, butylsulfinyl group, hexylsulfinyl group, octylsulfinyl group, etc., preferably methylsulfinyl group.

The "$C_1$–$C_8$ alkylsulfonyl group" means an alkylsulfonyl group having a carbon number of from 1 to 8, concretely methylsulfonyl group, ethylsulfonyl group, butylsulfonyl group, hexylsulfonyl group, octylsulfonyl group, etc., preferably methylsulfonyl group.

The "mono- or di-$C_1$–$C_8$ alkylamino group" means methylamino group, dimethylamino group, ethylamino group, propylamino group, diethylamino group, isopropylamino group, diisopropylamino group, dibutylamino group, butylamino group, isobutylamino group, sec-butylamino group, tert-butylamino group, pentylamino group, hexylamino group, heptylamino group, octylamino group, etc., preferably methylamino group, dimethylamino group, ethylamino group, diethylamino group or propylamino group, more preferably methylamino group or dimethylamino group.

The "mono- or di-$C_1$–$C_8$ alkylaminosulfonyl group" means methylaminosulfonyl group, dimethylaminosulfonyl group, ethylaminosulfonyl group, propylaminosulfonyl group, diethylaminosulfonyl group, isopropylaminosulfonyl group, diisopropylaminosulfonyl group, dibutylaminosulfonyl group, butylaminosulfonyl group, isobutylaminosulfonyl group, sec-butylaminosulfonyl group, tert-butylaminosulfonyl group, pentylaminosulfonyl group, hexylaminosulfonyl group, heptylaminosulfonyl group, octylaminosulfonyl group, etc., preferably methylaminosulfonyl group, dimethylaminosulfonyl group, ethylaminosulfonyl group, diethylaminosulfonyl group or propylaminosulfonyl group, more preferably methylaminosulfonyl group or dimethylaminosulfonyl group.

The "bis(alkoxycarbonyl)methyl group" means bis(methoxycarbonyl)methyl group, bis(ethoxycarbonyl)methyl group, etc., preferably bis(methoxycarbonyl)methyl group.

The "$C_1$–$C_{10}$ alkyl group" means a straight or branched carbon chain having a carbon number of from 1 to 10, e.g. methyl group, ethyl group, propyl group, isopropyl group, butyl group, isobutyl group, tert-butyl group, pentyl group, neopentyl group, isopentyl group, 1,2-dimethylpropyl group, hexyl group, isohexyl group, 1,1-dimethylbutyl group, 2,2-dimethylbutyl group, 1-ethylbutyl group, 2-ethylbutyl group, heptyl group, isoheptyl group, 1-methylhexyl group, 2-methylhexyl group, octyl group, 2-ethylhexyl group, nonyl group, decyl group, 1-methylnonyl group, etc., preferably a group having a carbon number of from 1 to 4, especially preferably methyl group or ethyl group.

The "$C_1$–$C_{10}$ alkylcarbonyl group" means a carbonyl group having straight or branched carbon chain having a carbon number of from 1 to 10, e.g. formyl group, acetyl group, propionyl group, butyryl group, isobutyryl group, valeryl group, isovaleryl group, pivaloyl group, hexanoyl group, heptanoyl group, octanoyl group, nonanoyl group, decanoyl group, etc., preferably a group having a carbon number of from 1 to 4, more preferably acetyl group or propionyl group.

The "$C_1$–$C_{10}$ alkylsulfonyl group" means an alkylsulfonyl group having a carbon number of from 1 to 10, concretely methylsulfonyl group, ethylsulfonyl group, propylsulfonyl group, isopropylsulfonyl group, butylsulfonyl group, isobutylsulfonyl group, pentylsulfonyl group, isopentylsulfonyl group, neopentylsulfonyl group, hexylsulfonyl group, heptylsulfonyl group, octylsulfonyl group, nonylsulfonyl group, decylsulfonyl group, etc., preferably a group having a carbon number of from 1 to 4, especially preferably methylsulfonyl group or ethylsulfonyl group.

The "$C_3$–$C_8$ cycloalkyl group" means a cycloalkyl group having a carbon number of from 3 to 8, concretely cyclopropyl group, cyclobutyl group, cyclopentyl group, cyclohexyl group, cycloheptyl group and cyclooctyl group, preferably cyclopropyl group. The "aryl group" means a hydrocarbon ring aryl group such as phenyl group and naphthyl group or a heteroaryl group such as pyridyl group and furyl group, preferably phenyl group.

The "$C_4$–$C_8$ cycloalkyl group" means a cycloalkyl group having a carbon number of from 4 to 8, concretely cyclobutyl group, cyclopentyl group, cyclohexyl group, cycloheptyl group or cyclooctyl group, preferably cyclopentyl group or cyclohexyl group.

The "aminoalkyl group" means a straight-chain alkyl group having a carbon number of from 1 to 8, concretely 8-aminooctyl group, 6-aminohexyl group, 4-aminobutyl group, 2-aminoethyl group or aminomethyl group, preferably 2-aminoethyl group or aminomethyl group.

The "mono- or di-alkylamino group" means methylamino group, dimethylamino group, ethylamino group, propylamino group, diethylamino group, isopropylamino group, diisopropylamino group, dibutylamino group, butylamino group, isobutylamino group, sec-butylamino group, tert-butylamino group, etc., preferably methylamino group, dimethylamino group, ethylamino group, diethylamino group, isopropylamino group or diisopropylamino group, more preferably ethylamino group, diethylamino group or isopropylamino group.

The "mono- or di-alkylaminoalkyl group" means methylaminoethyl group, dimethylaminoethyl group, ethylaminoethyl group, methylaminopropyl group, dimethylaminopropyl group, ethylaminopropyl group, diethylaminopropyl group, methylaminobutyl group, dimethylaminobutyl group, etc., preferably methylaminoethyl group, dimethylaminoethyl group or ethylaminoethyl group.

The "$C_1$–$C_{10}$ alkyl group" bonding to a nitrogen atom as the group Z means a straight or branched carbon chain having a carbon number of from 1 to 10, e.g. methyl group, ethyl group, propyl group, isopropyl group, butyl group, isobutyl group, tert-butyl group, pentyl group, neopentyl group, isopentyl group, 1,2-dimethylpropyl group, hexyl group, isohexyl group, 1,1-dimethylbutyl group, 2,2-dimethylbutyl group, 1-ethylbutyl group, 2-ethylbutyl group, heptyl group, isoheptyl group, 1-methylhexyl group, 2-methylhexyl group, octyl group, 2-ethylhexyl group, nonyl group, decyl group, 1-methylnonyl group, etc., preferably a group having a carbon number of from 1 to 4, especially preferably isopropyl group or propyl group.

The "arylcarbonyl group" means benzoyl group, 4-methoxybenzoyl group, 3-trifluoromethylbenzoyl group, etc., preferably benzoyl group.

The "aralkylcarbonyl group" is concretely benzylcarbonyl group, phenethylcarbonyl group, phenylpropylcarbonyl group, 1-naphthylmethylcarbonyl group, 2-naphthylmethylcarbonyl group, etc., preferably benzylcarbonyl group.

The "aralkyl group" is concretely benzyl group, phenethyl group, phenylpropyl group, 1-naphthylmethyl group, 2-naphthylmethyl group, etc., preferably benzyl group.

There is no particular restriction on the kind of the salt of the compound of the present invention provided that the salt is pharmacologically permissible, and the examples of the salts are hydrochloric acid salt, sulfuric acid salt, nitric acid salt, phosphoric acid salt, tartaric acid salt, maleic acid salt, succinic acid salt, malonic acid salt, glutaric acid salt, malic acid salt, adipic acid salt, acetic acid salt, propionic acid salt, hydrobromic acid salt, hydroiodic acid salt, methanesulfonic acid salt, 2-hydroxysulfonic acid salt and p-toluenesulfonic acid salt.

There is no particular restriction on the kind of the solvate of the compound of the present invention or its salt provided that the solvate is pharmacologically permissible, and hydrate, etc., are preferable examples.

Representative processes for the production of the compound of the present invention expressed by the formula (I) are described as follows.

When the starting compounds or reaction intermediates have substituents possible to exert influence on the reaction such as hydroxyl group, amino group and carboxyl group, the etherification reaction is carried out preferably after properly protecting such functional groups and the protecting group is eliminated after the reaction. Any protecting group ordinarily used for the protection of individual substituent can be used as the protecting group provided that the substituent exerts no adverse influence on the other part of the molecule during the protecting and deprotecting steps. The protecting groups for hydroxyl group are trialkylsilyl group, $C_1$–$C_4$ alkoxymethyl group, tetrahydropyranyl group, acyl group, $C_1$–$C_4$ alkoxycarbonyl group, etc., the protecting groups for amino group are $C_1$–$C_4$ alkoxycarbonyl group, benzyloxycarbonyl group, acyl group, etc., and the protecting groups for carboxyl group are $C_1$–$C_4$ alkyl group, etc. The deprotection reaction can be performed according to a process usually adopted to the protecting group.

The compounds containing oxygen atom as the group X among the nitrile compound used as a precursor of the compound of the present invention expressed by the formula (I) can be synthesized e.g. by the reaction shown by the following reaction formula (a-1).

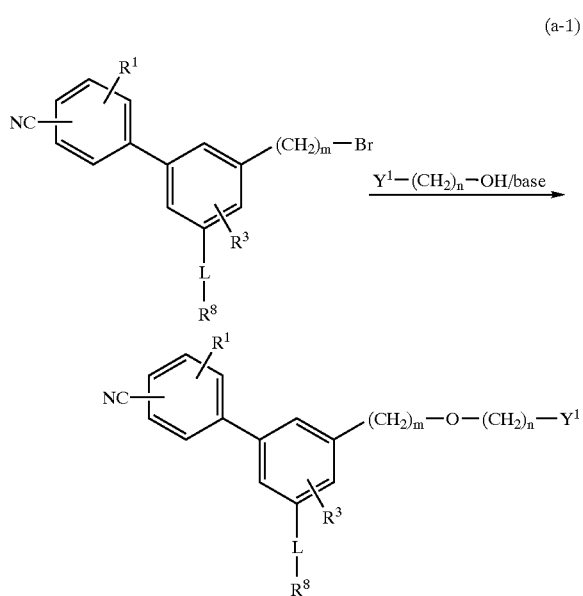

(a-1)

[in the reaction formula, the definitions of $R^1$, $R^3$, L, m and n are same as those described in the formula (I), $Y^1$, is a substituent Y defined in the formula (I) except for the group having a substituent Z of the structure expressed by the formula I-3 on the group Y, and $R^8$ is hydrogen atom, fluorine atom, chlorine atom, bromine atom, hydroxyl group (or its protected group), amino group (or its protected group) or $C_1$–$C_8$ alkoxy group].

Namely, a nitrile compound as a precursor of the compound of the present invention can be produced according to the above reaction formula (a-1) by mixing a biphenylalkyl bromide compound used as a starting raw material with an alcohol of formula $Y^1$—$(CH_2)_n$—OH in the presence of a base.

The compound containing oxygen atom as the group X among the nitrile compounds used as the precursor of the compound of the present invention expressed by the formula (I) can be synthesized by the reaction expressed by the following reaction formula (a-2).

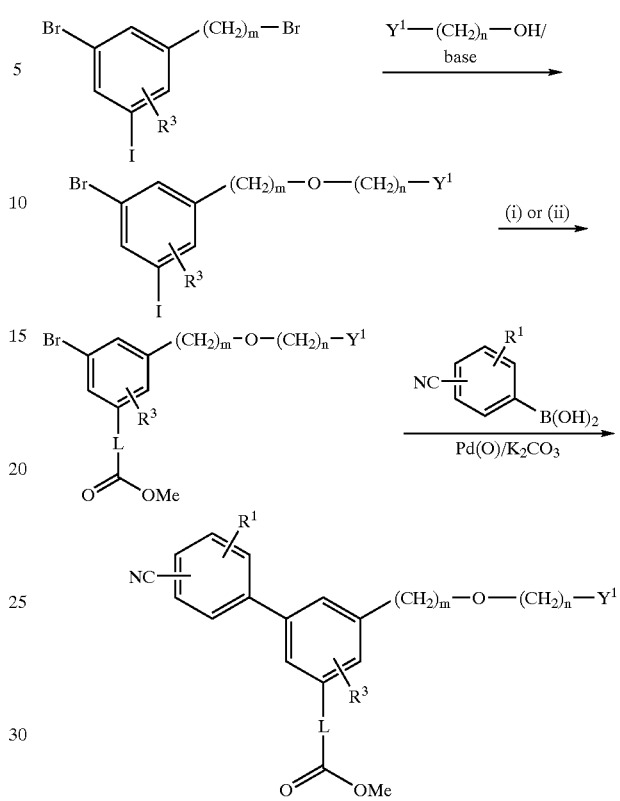

(a-2)

[in the reaction formula, the definitions of $R^1$, $R^3$, L, m and n are same as those of the formula (I), and $Y^1$ is a substituent Y defined in the formula (I) except for the group having a substituent Z of the structure expressed by the formula I-3 on the group Y].

Namely, the nitrile compound used as a precursor of the compound of the present invention can be synthesized by mixing 3-bromo-3-iodophenylalkyl bromide used as a starting raw material with an alcohol expressed by the formula $Y^1$—$(CH_2)_n$—OH in the presence of a base to form a 3-bromo-3-iodophenylalkyl ether compound, introducing a substituent —L—COOMe into the obtained ether compound by monocarbonylation or monoalkylation and subjecting the produced 3-bromophenylalkyl ether to coupling reaction with a cyanophenylboronic acid derivative.

The etherification reaction expressed in the 1st stage of the reaction formulas (a-1) and (a-2) is carried out by using an aliphatic ether such as tetrahydrofuran and diethyl ether, an aprotic hydrocarbon such as benzene and toluene, an aprotic polar solvent such as DMF and HMPA or their mixture. The base to be used in the reaction is a metal oxide such as barium oxide and zinc oxide, a metal hydroxide such as sodium hydroxide and potassium hydroxide, metal hydride such as sodium hydride, etc. The reaction proceeds usually by stirring at 0 to 100° C. for 3 to 72 hours. Preferably, the reaction is carried out in an anhydrous aliphatic ether such as THF and ether using sodium hydride at 20 to 80° C. for 8 to 36 hours.

The 2nd stage of the reaction formula (a-2) comprising the reaction to introduce a substituent —L—COOMe into the ether compound can be carried out by the following reactions (i) and (ii).

(i) Monocarbonylation reaction by the introduction of carbon monoxide (when L is a bond): The ether compound obtained by the 1st stage of the reaction formula (a-1) is dissolved in methanol, a bivalent palladium catalyst, a base such as a tertiary amine, e.g. triethylamine and as necessary a phosphine ligand such as triphenyl phosphine are added to the solution and the mixture is stirred in carbon monoxide atmosphere at room temperature or under heating for 3 to 48 hours to convert the iodine atom into methoxycarbonyl group. Preferably, the catalyst is bistriphenylphosphine palladium chloride or palladium acetate, the base is diisopropylethylamine or tributylaluminum and the reaction is carried out at 60 to 80° C. for 12 to 36 hours.

(ii) Monoalkylation reaction with an organozinc reagent (when L is a $C_1$–$C_4$ alkylene group): The ether compound obtained by the 1st stage of the reaction formula (a-1) is dissolved together with a zero-valent palladium catalyst such as tetrakistriphenylphosphine palladium into a solvent such as THF, DMF, benzene, toluene or their mixture, a THF solution of an alkylzinc reaction agent expressed by the formula I—Zn—L—COOMe is added to the solution and the mixture is stirred in carbon monoxide atmosphere at room temperature or under heating for 3 to 48 hours to convert the iodine into an alkyl group. Preferably, the reaction is carried out at 20–80° C. for 6 to 36 hours using tetrakistriphenylphosphine palladium as the catalyst and THF as the solvent.

The biphenylation reaction constituting the 3rd stage of the reaction formula (a-2) can be performed by reacting a monohalogenated compound with cyanophenyl boronic acid in the presence of a palladium catalyst. The reaction proceeds usually by stirring the monohalogenated compound obtained by the 2nd stage of the reaction formula (a-2), a bivalent palladium catalyst such as palladium acetate and further a base such as triethylamine and a triaryl phosphine in DMF under heating to obtain the objective cyanobiphenyl compound. The reaction is preferably carried out at 60 to 100° C. for 2 to 24 hours.

The compound having nitrogen atom as the group X among the nitrile compounds constituting the precursor of the compound of the present invention described by the formula (I) can be synthesized e.g. by the reaction of the following reaction formula (b-1) or (b-2).

(b-1)

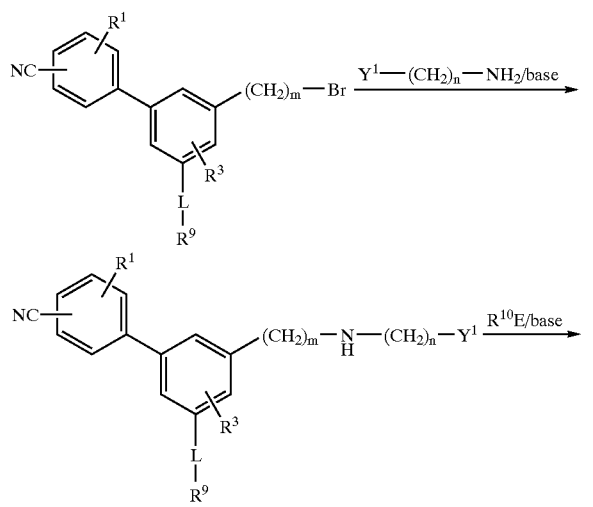

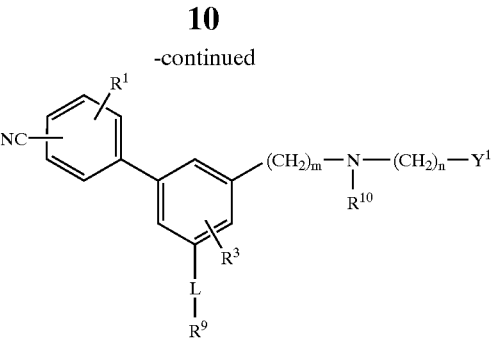

-continued

[in the reaction formula, the definitions of $R^1$, $R^3$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), $Y^1$ is a substituent Y defined in the formula (I) except for the group having a substituent Z of the structure expressed by the formula I-3 on the group Y, $R^{10}$ is the substituent $R^4$ defined in the formula (I) excluding hydrogen atom and aryl group, and E is an eliminable group such as chlorine, bromine, iodine, acyloxy group or sulfonyloxy group].

(b-2)

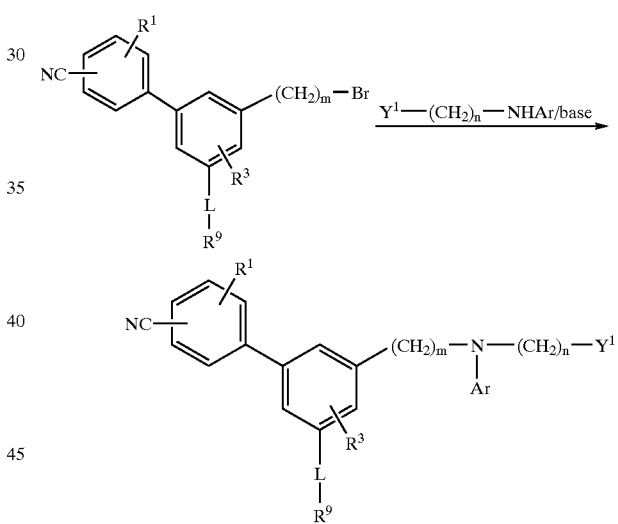

[in the reaction formula, the definitions of $R^1$, $R^3$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), $Y^1$ is a substituent Y defined in the formula (I) except for the group having a substituent Z of the structure expressed by the formula I-3 on the group Y, Ar is an aryl group, and E is an eliminable group such as chlorine, bromine, iodine, acyloxy group or sulfonyloxy group].

The N-alkylation reaction shown by the reaction formulas (b-1) and (b-2) can be carried out under known alkylation reaction conditions. Concretely, a secondary amine compound constituting the compound of the present invention is produced by reacting a biphenylalkyl bromide used as a raw material with an amine of formula $Y^1$—$(CH_2)_n$—$NH_2$ in the presence of an inorganic salt such as potassium carbonate or an amine such as a tertiary amine acting as a base and the obtained secondary amine compound can be converted to the tertiary amine as the compound of the present invention by reacting with an alkylation agent expressed by the formula $R^4$—E. The reaction is usually carried out by mixing the alkylation agent and the amine at an arbitrary ratio in a proper solvent and by stirring the mixture under cooling, at room temperature or under heating for 1 to 96 hours. The reaction is usually performed by using an inorganic salt such as potassium carbonate and sodium carbonate or an organic tertiary amine such as triethylamine and pyridine as the base and an alcohol such as methanol and ethanol, a hydrocarbon such as benzene and toluene, a solvent inert to the reaction such as THF, dioxane, acetonitrile DMF and DMSO or their mixture as the solvent at an (alkylation agent):(amine) ratio of 1:10 to 10:1. Preferably, the ratio of the alkylation agent to the amine is set to 1:5 to 1:1 and the reaction is carried out at room temperature or under heating for 2 to 24 hours.

The compound containing sulfur atom as the group X among the nitrile compounds constituting a precursor of the compound of the present invention expressed by the formula (I) can be synthesized e.g. by the reaction shown by the following reaction formula (c-1) or (c-2).

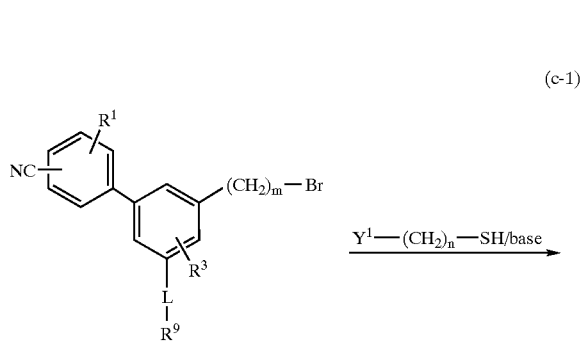
(c-1)

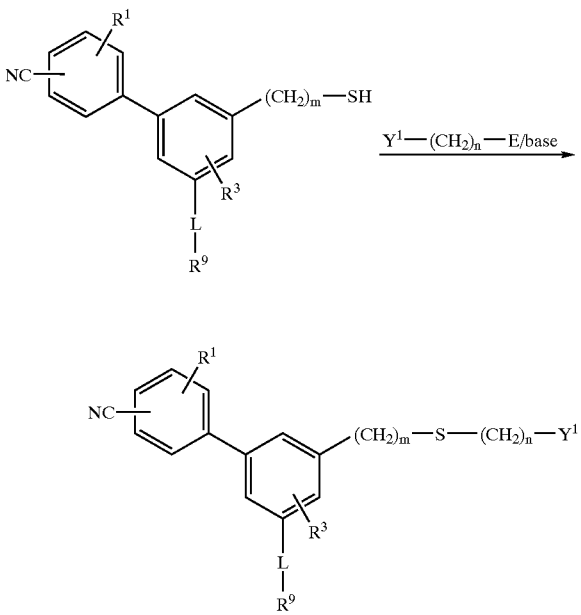
(c-2)

[in the reaction formula, the definitions of $R^1$, $R^3$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), $Y^1$ is a substituent Y defined in the formula (I) except for the group having a substituent Z of the structure expressed by the formula I-3 on the group Y, and E is an eliminable group such as chlorine, bromine, iodine or sulfonato group].

The thioetherification reaction expressed by the reaction formulas (c-1) and (c-2) can be carried out under known reaction conditions. Usually, the reaction is carried out by mixing an alkyl halide with a thiol at an arbitrary ratio in a proper solvent in the presence of a base such as sodium hydroxide or ammonia and stirring the mixture under cooling, at room temperature or under heating for 30 minutes to 96 hours. A solvent free from adverse effect on the reaction such as water, ethanol, DMF or toluene is used as the reaction solvent and the base is sodium hydroxide, ammonia, cesium carbonate, etc. The reaction is preferably carried out by mixing the alkyl halide with the thiol at a ratio of 1:5 to 5:1 and stirring the mixture at room temperature or under heating for 30 minutes to 24 hours.

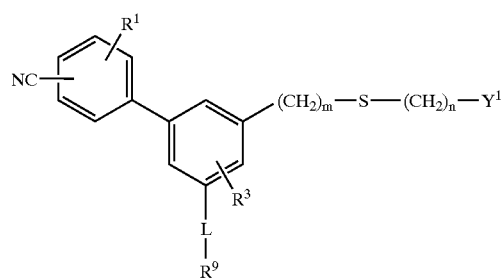

[in the reaction formula, the definitions of $R^1$, $R^3$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), $Y^1$ is a substituent Y defined in the formula (I) except for the group having a substituent Z of the structure expressed by the formula I-3 on the group Y, and E is an eliminable group such as chlorine, bromine, iodine or sulfonato group].

A compound having sulfoxide group or sulfone group as the group X among the compounds expressed by the formula (I) can be synthesized by the oxidation reaction of the obtained sulfide compound according to the following reaction formula (d).

(d)

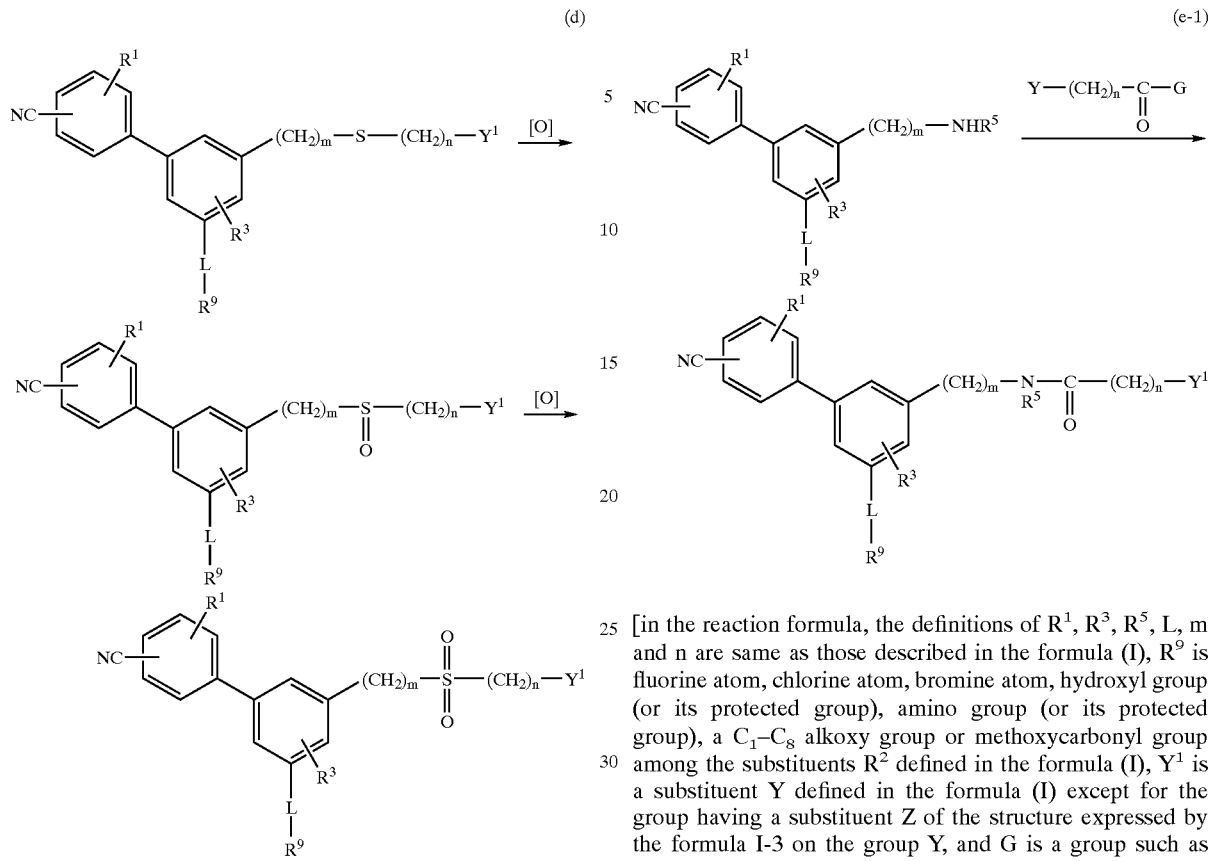

(e-1)

[in the reaction formula, the definitions of $R^1$, $R^3$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), and $Y^1$ is a substituent Y defined in the formula (I) except for the group having a substituent Z of the structure expressed by the formula I-3 on the group Y].

The oxidation reaction expressed by the reaction formula (d) can be carried out by the method described in the Experimental Chemistry Course (4th edition), 24, Organic Syntheses VI—Hetero-Element. Typical Metal Compound-, p.350–373 edited by the Chemical Society of Japan. The reaction is usually carried out by stirring a sulfide or a sulfoxide in water or an alcohol such as methanol using hydrogen peroxide, peracetic acid, meta-periodic acid salt, m-chloroperbenzoic acid, etc., as an oxidizing agent under cooling, at room temperature or under heating for 30 minutes to 24 hours. Preferably, the sulfoxide is produced at 0–20° C. in 30 to 12 hours and the sulfone is produced at 0–80° C. in 1 to 12 hours.

The compound containing amide bond as the group X among the nitrile compounds constituting a precursor of the compound of the present invention expressed by the formula (I) can be synthesized e.g. by the reaction shown by the following reaction formula (e-1) or (e-2).

[in the reaction formula, the definitions of $R^1$, $R^3$, $R^5$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), $Y^1$ is a substituent Y defined in the formula (I) except for the group having a substituent Z of the structure expressed by the formula I-3 on the group Y, and G is a group such as halogen, acyloxy group, p-nitrophenoxy group and hydroxyl group].

(e-2)

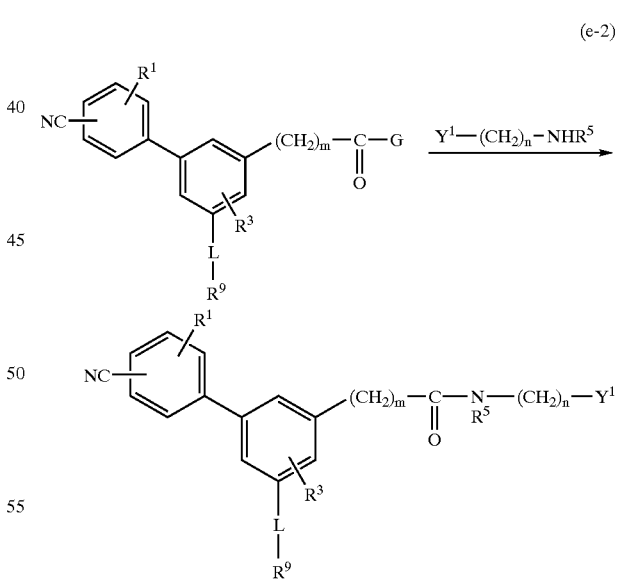

[in the reaction formula, the definitions of $R^1$, $R^3$, $R^5$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), $Y^1$ is a substituent Y defined in the formula (I) except for the group having a substituent Z of the structure expressed by the formula I-3 on the group Y, and G is a group such as halogen, acyloxy group, p-nitrophenoxy group and hydroxyl group].

The reaction of the above reaction formula (e-1) or (e-2) can be carried out under the known amidation reaction conditions. An amide compound is produced usually by mixing an active derivative of a carboxylic acid with an amine compound in a proper solvent in the presence of a base, followed with acylating the compound. The active derivative of carboxylic acid is an acid halide, an anhydride of a mixed acid, an active ester of p-nitrophenol, etc., and the reaction is carried out under cooling or at room temperature for 30 minutes to 24 hours. The reaction is preferably carried out by using a tertiary amine such as triethylamine as the base in a halogenated hydrocarbon such as dichloromethane, an aliphatic ether such as THF and diethyl ether, a solvent such as acetonitrile and DMF or their mixture at 0 to 20° C. for 1 to 18 hours.

The amide compound is producible also by the condensation reaction of an amine with a carboxylic acid in the presence of a condensing agent such as carbodiimide. In this case, the suitable solvent is DMF and a halogenated hydrocarbon such as chloroform and the condensing agent is preferably N,N-dicyclohexylcarbodiimide, 1-ethyl-(3-(N,N-dimethylamino)propyl)carbodiimide, carbonyl diimidazole, diphenylphosphoryl azide or diethylphosphoryl cyanide. The reaction is carried out usually under cooling or at room temperature for 2 to 48 hours.

The compound containing sulfonamide structure as the group X among the nitrile compounds constituting a precursor of the compound of the present invention expressed by the formula (I) can be synthesized e.g. by the reaction shown by the following reaction formula (f-1) or (f-2).

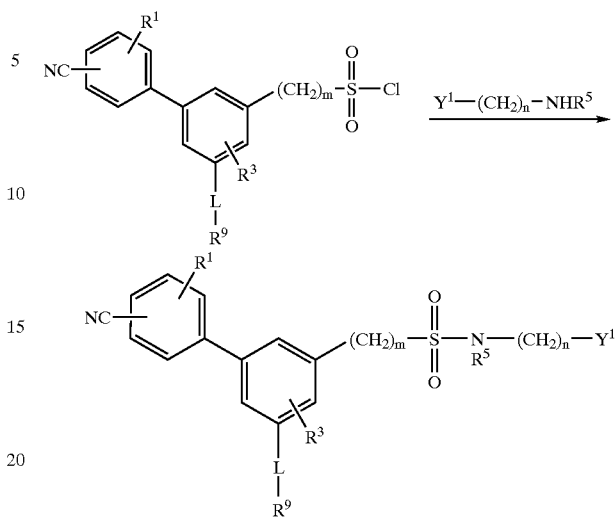

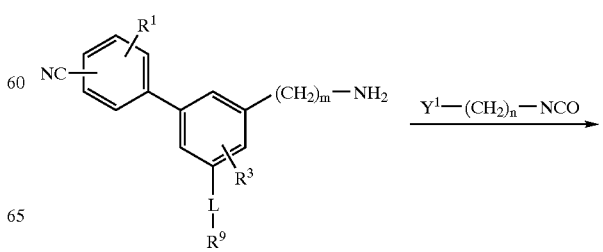

[in the reaction formula, the definitions of $R^1$, $R^3$, $R^5$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), and $Y^1$ is a substituent Y defined in the formula (I) except for the group having a substituent Z of the structure expressed by the formula I-3 on the group Y].

The reaction expressed by the reaction formulas (f-1) and (f-2) can be carried out by reacting an amine with an active derivative of a sulfonic acid in a proper solvent in the presence of a base to obtain the objective sulfonamide compound. The active derivative of sulfonic acid is preferably a sulfonyl halide and the reaction is carried out by using a tertiary amine such as triethylamine as the base in a halogenated hydrocarbon such as dichloromethane, an aliphatic ether such as THF or diethyl ether, a solvent such as acetonitrile or DMF or their mixture at 0 to 20° C. for 1 to 24 hours.

The compound containing urea structure as the group X among the nitrile compounds constituting a precursor of the compound of the present invention expressed by the formula (I) can be synthesized e.g. by the reaction shown by the following reaction formula (g).

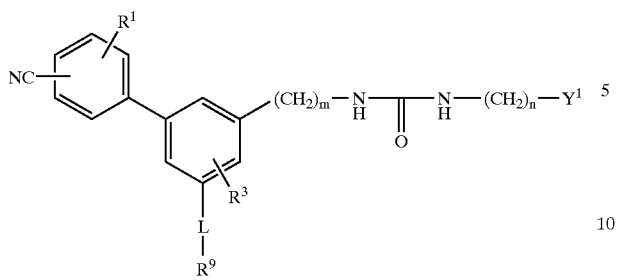
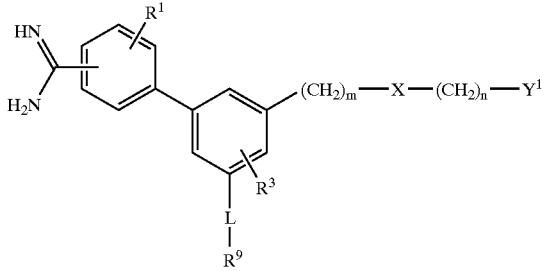

[in the reaction formula, the definitions of $R^1$, $R^3$, L, m and n are same as those described in the formula (I), $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), and $Y^1$ is a substituent Y defined in the formula (I) except for the group having a substituent Z of the structure expressed by the formula I-3 on the group Y].

Namely, the compound having urea structure as the group X can be produced by reacting an amine as a starting raw material with an isocyanate derivative in a proper solvent under cooling or heating. The solvent to be used in the reaction is DMF, THF, dioxane, dichloroethane, chloroform, acetonitrile, DMSO, benzene, toluene, etc.

The nitrile compound constituting a precursor of the compound of the present invention and produced by the above reaction formulas (a-1), (a-2), (b-1), (b-2), (c-1), (c-2), (d), (e-1), (e-2), (f-1), (f-2) and (g) can be converted to a benzamidine derivative which is a compound of the present invention by the amidination reaction shown by the following reaction formula (h).

(h)

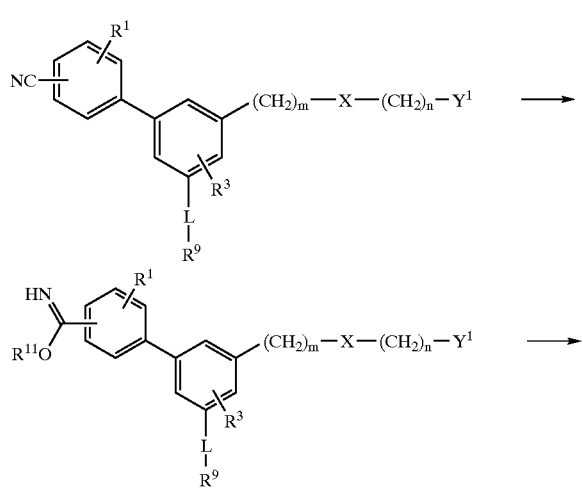

[in the reaction formula, the definitions of $R^1$, $R^3$, L, X, m and n are same as those described in the formula (I), $Y^1$ is a substituent Y defined in the formula (I) except for the group having a substituent Z of the structure expressed by the formula I-3 on the group Y, $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I), and $R^{11}$ is a $C_1$–$C_4$ alkyl group].

The amidination reaction is carried out under the reaction conditions shown by the following description (iii) or (iv).

(iii) The amidination reaction through imidation process using an alcohol solution of a hydrogen halide: The reaction to produce an imidate from a nitrile and an alcohol proceeds e.g. by the stirring of an alkoxymethylphenyl benzonitrile compound in the form of a solution dissolved in a $C_1$–$C_4$ alcohol ($R^{11}$OH) containing a hydrogen halide such as hydrogen chloride or hydrogen bromide. The reaction is usually carried out at −20 to +30° C. for 12 to 96 hours, preferably in a methanol or ethanol solution of hydrogen chloride at −10 to +30° C. for 24 to 72 hours. The reaction of an imidate with ammonia proceeds to form a benzamidine derivative (I) as the compound of the present invention by stirring an imidate in a solvent containing ammonia or an amine such as hydroxylamine, hydrazine or a carbamic acid ester and selected from a $C_1$–$C_4$ alcohol such as methanol and ethanol, an aliphatic ether solvent such as diethyl ether, a halogenated hydrocarbon solvent such as dichloromethane and chloroform or their mixture. The reaction is usually carried out at −10 to +50° C. for 1 to 48 hours, preferably in methanol or ethanol at 0 to 30° C. for 2 to 12 hours.

(iv) The amidination reaction through an imidate prepared by directly blowing a hydrogen halide: The reaction of a nitrile with an alcohol proceeds e.g. by dissolving a nitrile in an aliphatic ether such as diethyl ether, a halogenated hydrocarbon such as chloroform or an aprotic solvent such as benzene, adding an equivalent or excess amount of $C_1$–$C_4$ alcohol ($R^{11}$OH) to the solution, passing a hydrogen halide such as hydrogen chloride and hydrogen bromide through the mixture under stirring at −30 to 0° C. for 30 minutes to 6 hours, stopping the supply of the hydrogen halide and continuing the stirring at 0 to 50° C. for 3 to 96 hours. Preferably, hydrogen chloride is passed through a halogenated hydrocarbon containing equivalent or excess amount of methanol or ethanol under stirring at −10 to 0° C. for 1 to 3 hours, the supply of the hydrogen chloride is stopped and the product is stirred at 10 to 40° C. for 8 to 24 hours. The imidate produced by the above process can be converted to a benzamidine derivative (I) as the compound of the present invention by stirring in a solvent containing ammonia or an amine such as hydroxylamine, hydrazine or a carbamic acid ester and selected from a $C_1$–$C_4$ alcohol solvent such as methanol or ethanol, an aliphatic ether solvent such as diethyl ether, a halogenated hydrocarbon solvent such as chloroform or their mixture. The reaction is usually carried out at −20 to +50° C. for 1 to 48 hours, preferably in ethanol saturated with ammonia at 0 to 30° C. for 2 to 12 hours.

The compound having the substituent Y containing a substituent Z having the structure expressed by the formula I-3 among the compounds of the present invention expressed by the formula (I) can be produced by producing a benzamidine compound having a secondary amino group in the substituent Y by the reaction expressed by the above reaction formula (h), followed by the imidoylation reaction of the product according to the following reaction formulas (j-1) and (j-2).

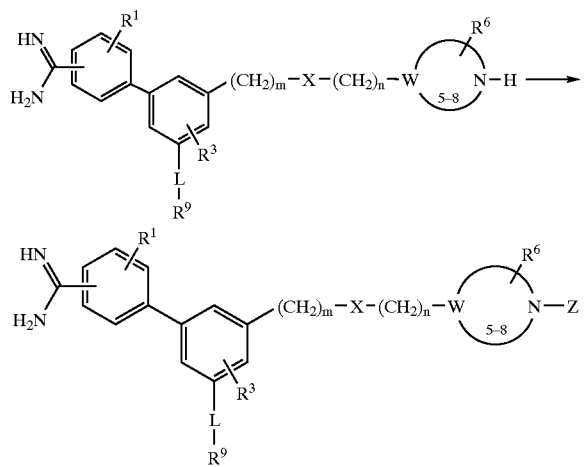

[in the reaction formula, the definitions of $R^1$, $R^3$, $R^6$, L, W, X, Z, m and n are same as those described in the formula (I), and $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I)].

[in the reaction formula, the definitions of $R^1$, $R^3$, $R^6$, L, W, X, Z, m and n are same as those described in the formula (I), and $R^9$ is fluorine atom, chlorine atom, bromine atom, hydroxyl group (or its protected group), amino group (or its protected group), a $C_1$–$C_8$ alkoxy group or methoxycarbonyl group among the substituents $R^2$ defined in the formula (I)].

The imidoylation reaction proceeds by mixing and stirring a benzamidine compound having a secondary amino group in the substituent Y together with an equivalent or excess amount of an imidate in water, a $C_1$–$C_4$ alcohol such as methanol or ethanol, an aliphatic ether such as diethyl ether, a halogenated hydrocarbon such as chloroform, a polar solvent such as DMF or DMSO or their mixture in the presence of a base. The reaction is usually carried out for 1 to 24 hours at room temperature. The base to be used in the above reaction is N-methylmorpholine, triethylamine, diisopropylethylamine, sodium hydroxide, potassium hydroxide, etc.

The compound having carboxyl group as the group $R^2$ among the compounds expressed by the formula (I) can be produced by the ester hydrolysis of a compound having methoxycarbonyl group as the group $R^9$ among the benzamidine compounds produced by the above reaction formulas (h), (j-1) and (j-2). The hydrolysis reaction can be carried out under basic condition, acidic condition or neutral condition at need. The base to be used in the reaction under basic condition is sodium hydroxide, potassium hydroxide, lithium hydroxide, barium hydroxide, etc., the acid for the acidic reaction condition is hydrochloric acid, sulfuric acid, a Lewis acid such as boron trichloride, trifluoroacetic acid, p-toluenesulfonic acid, etc., and the examples of the substances to be used in the reaction under neutral condition are halogen ions such as lithium iodide and lithium bromide, alkali metal salts of a thiol and selenol, iodotrimethylsilane and enzymes such as an esterase. The solvent for the reaction is a polar solvent such as water, alcohol, acetone, dioxane, THF, DMF and DMSO or their mixture. The reaction is carried out usually at room temperature or under heating for 2 to 96 hours. The preferable conditions of the reaction temperature and reaction time, etc., are dependent on the reaction condition and properly selected according to conventional method.

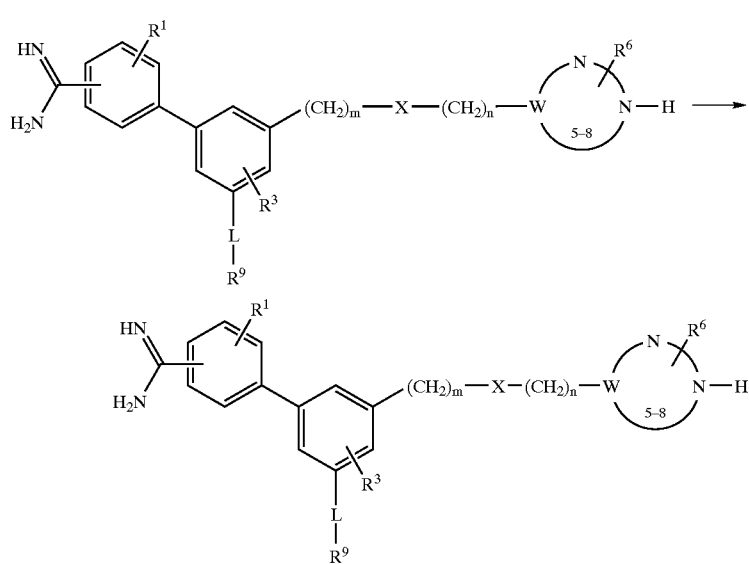

(j-2)

The carboxyl group of the compound having carboxyl group as the substituent $R^2$ and produced by this process can be converted to other ester group by the following methods of (v), (vi) and (vii).

(v) Conversion of carboxyl group into an alkoxycarbonyl group: The carboxyl group of a compound having carboxyl group as the substituent $R^2$ among the compounds expressed by the formula (I) can be converted into an alkoxycarbonyl group by reacting the compound with equivalent or excess amount of an alkylation agent (e.g. acyloxymethyl chloride such as acetoxymethyl chloride and pivaloyloxymethyl chloride, allyl chloride and benzyl chloride) in a halogenated hydrocarbon such as dichloromethane, an aliphatic ether such as THF, an aprotic polar solvent such as DMF or their mixture in the presence of a tertiary amine such as triethylamine and diusopropylethylamine at −10 to +80° C. for 1 to 48 hours. The reaction is preferably carried out by using equivalent or small excess amount of the alkylation agent in the presence of diusopropylethylamine at 20 to 60° C. for 2 to 24 hours.

(vi) Conversion of carboxyl group into an aralkoxycarbonyl group: The carboxyl group of a compound having carboxyl group as the substituent $R^2$ among the compounds expressed by the formula (I) can be converted into an aralkoxycarbonyl group by reacting the compound with equivalent or excess amount of an alcohol such as benzyl alcohol in a halogenated hydrocarbon such as dichloromethane in the presence of an acid catalyst such as hydrochloric acid, sulfuric acid and sulfonic acid. The reaction is carried out usually at room temperature or under heating for 1 to 72 hours, preferably by using equivalent or small excess amount of an alcohol in the presence of diisopropylethylamine at 20 to 60° C. for 2 to 24 hours.

(vii) Conversion of carboxyl group into an aryloxycarbonyl group: The carboxyl group of a compound having carboxyl group as the substituent $R^2$ among the compounds expressed by the formula (I) can be converted into an aryloxycarbonyl group by reacting the compound with equivalent or excess amount of a hydroxyl-containing aromatic compound such as phenol using an aliphatic ether such as diethyl ether as a solvent in the presence of a condensation agent such as dicyclohexylcarbodiimide. The reaction is carried out usually at 0 to 50° C. for 1 to 48 hours, preferably at room temperature for 3 to 24 hours.

The carboxyl group of a compound having a carboxyl group as the $R^2$ group can be converted into carbamoyl group by conventional method such as the conversion of the carboxyl group to an acid halide with oxalyl chloride, etc., followed by the reaction of the product with ammonia water. Similarly, the acid halide can be converted to N-methyl-N-methoxycarbamoyl group by reacting with N-methyl-N-methoxyamine and the product can be converted further to an alkylcarbonyl group by the reaction with various kinds of alkylmagnesium reactants.

For a compound having amidino group as the substituent A among the compounds of the present invention synthesized by the above methods, various carbonyl groups can be introduced to one of the nitrogen atoms constituting the amidino group by the methods shown by (ix), (x) and (xi).

(ix) Aryloxycarbonylation reaction of amidino group: An aryloxycarbonyl group can be introduced to one of the nitrogen atoms constituting the amidino group of a compound having amidino group as the substituent A among the compounds expressed by the formula (I) by stirring the compound together with equivalent or excess amount of an aryl chloroformate such as phenyl chloroformate in the presence of a base such as sodium hydroxide or potassium hydroxide in a mixture of water and a halogenated hydrocarbon such as dichloromethane. The reaction is carried out usually at −10 to +40° C. for 3 to 48 hours, preferably using equivalent or small excess amount of an aryl chloroformate at 0–30° C. for 6 to 24 hours.

(x) Alkoxycarbonylation reaction of amidino group: An alkoxycarbonyl group can be introduced to one of the nitrogen atoms constituting the amidino group of a compound having amidino group as the substituent A among the compounds expressed by the formula (I) by reacting the compound with equivalent or excess amount of p-nitrophenyl alkylcarbonate in an anhydrous solvent such as THF and DMF in the presence of a metal hydride such as sodium hydride or a base such as a tertiary amine at −10 to +30° C. for 3 to 48 hours. Preferably, the reaction is carried out by using equivalent to small excess amount of a p-nitrophenyl alkylcarbonate in the presence of a tertiary amine such as triethylamine or diusopropylethylamine at −10 to +40° C. for 6 to 24 hours.

(xi) Arylcarbonylation reaction of amidino group: An arylcarbonyl group can be introduced to one of the nitrogen atoms constituting the amidino group of a compound having amidino group as the substituent A among the compounds expressed by the formula (I) by reacting the compound with equivalent or excess amount of an aromatic carboxylic acid chloride such as benzoyl chloride in a halogenated hydrocarbon such as methylene chloride, a solvent such as THF, DMF or pyridine or their mixture in the presence of a base such as an amine at −10 to +30° C. for 1 to 48 hours. Preferably, the reaction is carried out by using equivalent to small excess amount of an aromatic carboxylic acid chloride in the presence of an amine such as triethylamine or diusopropylethylamine at −10 to +40° C. for 2 to 24 hours.

The compound expressed by the formula (I) can be produced also by an arbitrary combination of known processes usually adoptable by persons skilled in the art such as etherification, amidination, hydrolysis, alkylimidoylation, amidation and esterification.

The alkoxymethylphenylbenzamidine derivative I produced by the above method can be separated and purified by conventional methods such as extraction, precipitation, fractional chromatography, fractional crystallization and recrystallization. The pharmacologically permissible salt of the compound of the present invention can be produced by the conventional salt-forming reaction.

The medicinal composition of the present invention is characterized by the property to reduce the contact of the compound of the present invention with components of bile or pancreatic juice secreted in the duodenum.

The reduction of the contact of the compound of the present invention with the components of bile or pancreatic juice means that the contact of the medicinal composition of the present invention with the components of bile or pancreatic juice is reduced compared with a composition usually taking a solution state in the stomach or a conventional oral administration drug quickly releasing the active component in the stomach.

The composition of the present invention can avoid the suppression of the absorption of the compound by reducing the contact of the compound of the present invention with the components of the bile or pancreatic juice.

A release-site regulating preparation is a preferable embodiment of the medicinal composition of the present invention.

There is no particular restriction on the releasing mechanism of such release-site regulating preparation provided that the medicinal composition can old the compound in the medicinal composition at least down to the duodenum to prevent the diffusion of the compound in the digestive tract and release the compound when the medicinal composition reaches the duodenum or the following small intestine or large intestine by its physiological condition or by a preparatorily integrated time-dependent mechanism. Preferable examples of the medicinal composition are shown below.

Medicinal Composition (1)

A medicinal composition produced by coating the compound of the present invention with a pH-dependently soluble enteric polymer.

Medicinal Composition (2)

A medicinal composition containing the compound of the present invention and a disintegrant, partly or totally covered its surface with a water-insoluble and water-permeable substance and having a mechanism to cause the collapse or opening after 0.5 to 5 hours when brought into contact with water.

Medicinal Composition (3)

A medicinal composition produced by coating the compound of the present invention with a material decomposable by enteric bacteria indigenous to the lower part of the small intestine to the large intestine.

These medicinal compositions (1) to (3) are explained in more detail.

The medicinal composition (1) is produced by coating a constituent component containing the compound of the present invention with a pH-dependently soluble enteric polymer, i.e. an enteric polymer resistant to dissolution below pH 4.5 and soluble at pH 4.5 or above.

The pH-dependent enteric polymer is, for example, anionic polymers such as hydroxypropyl methylcellulose acetate succinate, hydroxypropyl methylcellulose phthalate, carboxymethyl ethylcellulose, cellulose acetate phthalate, cellulose acetate trimellitate, polyvinyl acetate phthalate and methacrylic acid copolymer.

The medicinal composition (2) is a composition containing the compound of the present invention and a disintegrant and partly or totally covered its surface with a layer composed of a water-insoluble and water-permeable substance. The swelling of the disintegrant takes place by the water permeated through the layer to cause the collapse or burst of the medicinal composition after the lapse of a prescribed period. The layer composed of the water-insoluble and water-permeable substance does not pass the compound.

The prescribed period means the time necessary to reach the medicinal composition to the duodenum having the opening of common bile duct to discharge the bile juice and pancreatic juice at high concentration or to pass the composition through the duodenum. The period is especially dependent upon the time to discharge the composition from the stomach. The discharging time from the stomach is considerably dependent upon the ingestion condition of food and the time of from several minutes to 24 hours is reported by a literature (Biopharmaceutics of Administered Drugs; P. Macheras, C. Reppas and J. B. Dressman; p89–p123; Ellis Horwood). When the state of the medicinal composition is between a suspension and a solid, the prescribed period is specified to 0.5 to 4.5 hours taking consideration of the fact that the discharging period from the stomach is about 0.5 to 4.5 hours in the case of administering to an empty stomach or after a light meal.

Preferable examples of the water-insoluble and water-permeable substance are ethylcellulose and cellulose acetate.

The disintegrant is preferably e.g. cellulose, cellulose lower alkyl ether, starch or its derivative.

The medicinal composition (3) is a composition produced by coating the compound of the present invention with a material decomposable by enteric bacteria indigenous to the lower part of the small intestine to the large intestine and releases the compound at the lower part of the digestive tract by the decomposition of the coating material with the enteric bacteria.

The enteric bacteria mean bacteria indigenous mainly to the lower part of the small intestine to the large intestine.

The material to be decomposed by the enteric bacteria is preferably an azo-containing segmented polyurethane, chitosan, etc.

Each of the medicinal compositions (1), (2) and (3) may be incorporated with a base foamable by the generation of carbon dioxide gas when the environment reaches a prescribed physical condition or after the lapse of a prescribed period.

Preferable example of the base to generate carbon dioxide gas is a combination of sodium bicarbonate with citric acid, tartaric acid, fumaric acid or heir salts.

The medicinal composition of the present invention may be further incorporated as necessary with a pharmacologically permissible excipient.

The administration rate of the compound of the present invention depends upon the kind of disease, administration method, symptom of the patient, age, sex, body weight, etc., and generally the rate is 1 to 1,000 mg/day/head, preferably 10 to 300 mg/day/head by oral administration.

EXAMPLES

The present invention is described in more detail in the following Examples, which do not restrict the scope of the invention.

Comparative Example 1

An aqueous solution (1.67 mg/mL) of 3-(3-amidinophenyl)-5-[(1-acetimidoyl-4-piperidinyl)methylaminomethyl]benzoic acid (hereinafter referred to as compound (A)) was administered to four fasted crab-eating monkeys of 5.5 to 7.0 kg body-weight at a rate of 5 mg/kg (corresponding to 3 mL/kg of the solution) and about 2 mL each of blood was collected at 7 points, i.e. immediately before the administration of the compound (A) and 0.5, 1, 2, 4, 8 and 10 hours after the administration. The plasma was separated and the concentration of the compound (A) was determined by LC/MS. The AUC (area under the curve of concentration in plasma vs. time) and Cmax (maximum concentration in plasma) were calculated as pharmacokinetic parameters by a moment analysis program. The results are collectively shown in the Table 1.

Example 1

The following experiments were performed by cross-over method using four crab-eating monkeys same as those used in the Comparative Example 1.

Powder of the compound (A) was encapsulated together with an excipient in a hard capsule made of M-type hydroxypropylmethyl cellulose acetate succinate (HPMCAS) (AQOAT; product of Shin-Etsu Chemical Co., Ltd.) having pH dependency and dissolving in the intestines. The capsules were administered to four fasted crab-eating monkeys of 5.5 to 7.0 kg body-weight at a rate of 5 mg/kg and about 2 mL each of blood was collected at 7 points, i.e. immediately before the administration of the compound (A) and 0.5, 1, 2, 4, 8 and 10 hours after the administration. The plasma was separated and the concentration of the compound (A)

was determined by LC/MS. The AUC and Cmax were calculated by the method same as the Comparative Example 1 and the results are collectively shown in the Table 1.

TABLE 1

| Pharmacokinetic parameters | AUC (∞) mg.hr/L | Cmax mg/L |
|---|---|---|
| Comparative Example 1 | 0.782 | 0.147 |
| Example 1 | 1.179 | 0.112 |

Comparative Example 1: Aqueous solution of the compound (A)
Example 1: Enteric capsule containing the compound (A)

Comparison between the Comparative Example 1 and the Example 1 revealed that the value of Cmax was larger in the Comparative Example 1 while that of AUC was large in the Example 1 and the absorptivity of the compound (A) was larger in the Example 1, suggesting that the absorption of the composition (aqueous solution) of the Comparative Example was suppressed by the contact with the components in the bile or pancreatic juice and that the composition (enteric capsule) of the Example 1 achieved decreased suppression of absorptivity by avoiding the contact with the components in the bile or pancreatic juice.

Comparative Example 2

A tablet containing 3-(3-amidinophenyl)-5-[(1-acetimidoyl-4-piperidinyl)methylaminomethyl]benzoic acid (hereinafter referred to as compound (A)) was prepared as a comparative example by the following method. Namely, 12.50 grams of the compound (A), 114.25 grams of lactose (Dilactose R) and 2.6 grams of croscarmellose sodium (AcDisol, product of Asahi Chemical Industry) were mixed for 2 minutes with a high-speed agitation granulator (FDG-C5, product of Fukae Industry), added with 0.65 gram of magnesium stearate and mixed for 10 seconds. The mixed powder was tableted with a single-shot tableting machine (KORSCH) to obtain a tablet (uncoated tablet) having a principal drug content of 11.5 mg/tablet, an average weight of 131.3 mg and a diameter of 7 mm.

The obtained uncoated tablet was administered to beagle dogs and the change of the drug concentration in plasma was measured. A suspension of loperamide hydrochloride was orally administered to four fasted beagle dogs at a rate of 0.12 mg/mL/kg together with 15 mL of ion-exchanged water and each dog was administered with two uncoated tablets each containing 11.5 mg of the drug after 30 minutes and allowed to drink 20 mL of ion-exchanged water. Blood was collected at 0.5, 1, 1, 2, 3, 4, 5, 6, 8, 10 and 12 hours after the administration and the drug concentration in plasma was determined. The pharmacokinetic parameters were determined by moment analysis using the plasma concentration data as a base. The results are shown in the Table 2. The Tmax (time to reach Cmax) of the drug was 1 hour, the Cmax was 0.318 mg/L and the AUC(∞) was 1.29 mg.hr/L.

Example 2

A mixture produced by mixing 28.8 grams of the compound (A), 263.7 grams of lactose and 2.6 grams of croscarmellose sodium by a high-speed agitation granulator for 2 minutes was added with 0.65 gram of magnesium stearate and mixed for 10 seconds. The mixed powder was tableted with a single-shot tableting machine to obtain a tablet of 7 mm diameter.

The produced tablet was coated with a coating liquid composed of 554.1 grams of purified water, 30.0 grams of hydroxypropylmethyl cellulose acetate succinate (AS-L-F type, product of Shin-Etsu Chemical Co., Ltd.), 6.0 grams of triethyl citrate (citroflex 2, SC-60), 9.0 grams of talc (product of Matsumura Sangyo Co.) and 0.9 gram of sodium laurylsulfate (product of Nikko Chemical Co.) by a coating machine (HCT-MINI, product of Freund Industrial Co.) to obtain an enteric coating tablet constituting the Example 2. The charged amount of the uncoated tablet was 250 grams and the heater temperature was set to 60° C. The content of the compound (A) in the obtained enteric coating tablet was 11.5 mg/tablet.

The effect of the enteric coating was confirmed by the following dissolution test. The tablets were put into 900 mL of the first fluid of the Japanese Pharmacopeia (pH 1.2), a buffer solution of pH 6.0 and the second fluid of the Japanese Pharmacopeia (pH 6.8) one for each fluid and the dissolution of the compound (A) was measured at 37° C. and 50 rpm. The dissolution of the compound (A) was unobservable in the first fluid of the Japanese Pharmacopeia even after 5 hours. In the buffer solution of pH 6.0, the dissolution ratio of the compound (A) was about 20% after 15 minutes and about 100% after 30 minutes. In the second fluid of the Japanese Pharmacopeia, the dissolution ratio of the compound (A) was about 70% after 15 minutes and about 100% after 30 minutes.

The experiment on the tablet of the Comparative Example 2 revealed the dissolution of about 100% of the compound (A) after 30 minutes in the first fluid of the Japanese Pharmacopeia (pH 1.2).

The enteric tablet obtained by the above Example 2 and quickly dissolving at pH 6 or above was administered to beagle dogs and the change of the drug concentration in plasma was measured. A suspension of loperamide hydrochloride was orally administered to four fasted beagle dogs at a rate of 0.12 mg/mL/kg together with 15 mL of ion-exchanged water and each dog was administered with two enteric tablets each containing 11.5 mg of the drug after 30 minutes and allowed to drink 20 mL of ion-exchanged water. Blood was collected at 0.5, 1, 2, 3, 4, 5, 6, 8, 10 and 12 hours after the administration and the drug concentration in plasma was determined. The pharmacokinetic parameters were determined by moment analysis using the data as a base. The results are shown in the Table 2. The Tmax of the drug was 1 hour, the Cmax was 0.341 mg/L and the AUC(∞) was 1.38 mg.hr/L. The Auc was increased and the retention time of the estimated effective blood concentration was prolonged compared with the Comparative Example 2.

TABLE 2

| PK Parameter | AUC mg.hr/L | Cmax mg/L | Tmax hr |
|---|---|---|---|
| Comparative Example 2 | 1.29 | 0.318 | 1.0 |
| Example 2 | 1.38 | 0.341 | 1.0 |

Comparative Example 2: Compound A tablet (uncoated tablet)
Example 2: Compound A tablet (enteric coating, quick releasing)

Comparison between the Comparative Example 2 and the Example 2 revealed that the absorbability of the composition of the Example 2 was higher because the values of AUC and Cmax were larger in the Example 2 compared with the Comparative Example 2. The fact suggests that the suppression of the absorption of the compound A caused by the contact with the components in the bile or pancreatic juice is avoided by the administration of the compound in the form of an enteric coating tablet.

What is claimed is:

1. A medicinal composition containing one or more compounds selected from the group consisting of compounds represented by formula (I), salts of these compounds, solvates of these compounds and solvates of these salts and a carrier, and wherein the composition is capable of reducing contact of the said compounds with components in bile or pancreatic juice.

Formula (I)

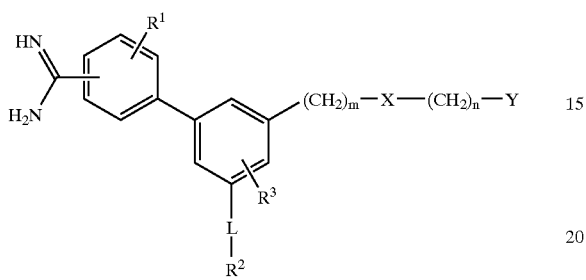

wherein:
- $R^1$ is hydrogen atom, fluorine atom, chlorine atom, bromine atom, hydroxyl group, amino group, nitro group, a $C_1$–$C_8$ alkyl group or a $C_1$–$C_8$ alkoxy group,
- L is direct bond or a $C_1$–$C_4$ alkylene group,
- $R^2$ is fluorine atom, chlorine atom, bromine atom, hydroxyl group, amino group, a $C_1$–$C_8$ alkoxy group, carboxyl group, a $C_1$–$C_8$ alkoxycarbonyl group, an aryloxycarbonyl group, an aralkoxycarbonyl group, carbamoyl group, wherein the nitrogen atom of the carbamoyl group may be substituted with mono- or di-$C_1$–$C_8$ alkyl group or may be the nitrogen atom of an amino acid, a $C_1$–$C_8$ alkylcarbonyl group, a $C_1$–$C_8$ alkylsulfenyl group, a $C_1$–$C_8$ alkylsulfinyl group, a $C_1$–$C_8$ alkylsulfonyl group, a mono- or di-$C_1$–$C_8$ alkylamino group, a mono- or di-$C_1$–$C_8$ alkylaminosulfonyl group, sulfo group, phosphono group, bis(hydroxycarbonyl)methyl group, a bis(alkoxycarbonyl)methyl group or 5-tetrazolyl group,
- $R^3$ is hydrogen atom, fluorine atom, chlorine atom, bromine atom, hydroxyl group, amino group, nitro group, a $C_1$–$C_8$ alkyl group, a $C_1$–$C_8$ alkoxy group, carboxyl group or a $C_1$–$C_8$ alkoxycarbonyl group,
- X is a group of the formulas —O—, —S—, —SO—, —$SO_2$—, —NH—CO—NH—, —N($R^4$)—, —CO—N($R^5$)—, —N($R^5$)—CO—, —N($R^5$)—$SO_2$— or —$SO_2$—N($R^5$)—, wherein:
- $R^4$ is hydrogen atom, a $C_1$–$C_{10}$ alkyl group, a $C_1$–$C_{10}$ alkylcarbonyl group, a $C_1$–$C_{10}$ alkylsulfony) group, a $C_3$–$C_8$ cycloalkyl group or an aryl group,
- $R^5$ is hydrogen atom, a $C_1$–$C_{10}$ alkyl group, a $C_3$–$C_8$ cycloalkyl group or an aryl group, and wherein the alkyl groups represented by $R^4$ and $R^5$ may be substituted with an aryl group, hydroxyl group, amino group, a halogen atom, a $C_1$–$C_8$ alkoxy group, carboxyl group, a $C_1$–$C_8$ alkoxycarbonyl group, an aryloxycarbonyl group, an aralkoxycarbonyl group, carbamoyl group or 5-tetrazolyl group,
- Y is a 6-membered ring group of the following formula I-1

Formula (I-1)

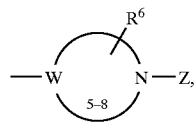

wherein:
- the methylene group of the ring system may be replaced with a carbonyl group and an unsaturated bond may be present in the ring,
- $R^6$ is hydrogen atom, fluorine atom, chlorine atom, bromine atom, hydroxyl group, amino group, nitro group, a $C_1$–$C_8$ alkyl group or a $C_1$–$C_8$ alkoxy group,
- W is C—H,
- Z is hydrogen atom, a $C_1$–$C_{10}$ alkyl group which may be substituted with hydroxyl group, excluding the case of a $C_1$ alkyl group, amino group, a $C_1$–$C_8$ alkoxy group, excluding the case of a $C_1$ alkyl group, carboxyl group, a $C_1$–$C_8$ alkoxycarbonyl group, an aryloxycarbonyl group or an aralkoxycarbonyl group, a $C_1$–$C_8$ alkylcarbonyl group, an arylcarbonyl group, an aralkylcarbonyl group, amidino group or a group of the following formula I-3

Formula (I-3)

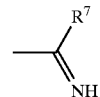

wherein:
- $R^7$ is a $C_1$–$C_8$ alkyl group which may be substituted with hydroxyl group or a $C_1$–$C_8$ alkoxy group, an aralkyl group or an aryl group,
- m is an integer of from 1 to 3, and
- n is an integer of from 0 to 3.

2. The medicinal composition according to claim 1 wherein the compounds are not released until the composition reaches the duodenum, the remainder of the small intestine or the large intestine.

3. The medicinal composition according to claim 1 or 2 wherein the medicinal composition is coated with an enteric polymer resistant to dissolution below pH 4.5 and soluble at pH 4.5 or above.

4. The medicinal composition according to claim 3 wherein said enteric polymer is one or more kinds selected from the group consisting of hydroxypropylmethyl cellulose acetate succinate, hydroxypropylmethyl cellulose phthalate, carboxymethyl ethylcellulose, cellulose acetate phthalate, cellulose acetate trimellitate, polyvinyl acetate phthalate and methacrylic acid copolymer.

5. The medicinal composition according to claim 1 or 2 wherein the medicinal composition additionally contains a disintegrant, and is coated totally or partly with a water-insoluble and water-permeable substance, and wherein the coated composition has a mechanism to destroy or open the coated composition upon contact with water for 0.5 to 4.5 hours.

6. The medicinal composition according to claim 1 or 2 wherein said compound is coated with a material decomposable by enteric bacteria indigenous to the lower part of the small intestine and to the large intestine.

* * * * *